(12) United States Patent
Ho et al.

(10) Patent No.: US 9,822,101 B1
(45) Date of Patent: Nov. 21, 2017

(54) PYRAZOLE COMPOUNDS

(71) Applicant: Eli Lilly and Company, Indianapolis, IN (US)

(72) Inventors: Koc Kan Ho, Shanghai (CN); Weiqiang Zhan, Shanghai (CN); Jingye Zhou, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/535,817

(22) PCT Filed: Feb. 11, 2016

(86) PCT No.: PCT/US2016/017466
§ 371 (c)(1),
(2) Date: Jun. 14, 2017

(87) PCT Pub. No.: WO2016/133770
PCT Pub. Date: Aug. 25, 2016

(30) Foreign Application Priority Data

Feb. 18, 2015  (CN) ................. PCT/CN2015/073236

(51) Int. Cl.
*C07D 403/14* (2006.01)
*A61K 31/506* (2006.01)

(52) U.S. Cl.
CPC .......... *C07D 403/14* (2013.01); *A61K 31/506* (2013.01)

(58) Field of Classification Search
None
See application file for complete search history.

(56) References Cited

FOREIGN PATENT DOCUMENTS

| CN | 103626775 A | 3/2014 |
|---|---|---|
| WO | 2010/065879 | 6/2010 |
| WO | 2015/089800 | 6/2015 |

*Primary Examiner* — Kamal Saeed

(74) *Attorney, Agent, or Firm* — R. Craig Tucker; MaCharri Vorndran-Jones

(57) ABSTRACT

This invention relates to pyrazole compounds or pharmaceutically acceptable salts thereof. Compounds of this invention are inhibitors of methionine aminopeptidase 2 (MetAP2) and dipeptidyl peptidase-4 (DPP-4). MetAP2 is a metalloproteinase that cleaves initiator methionine from nascent peptide emerging from the ribosomes. WO 2010/065879 reports small molecule MetAP2 inhibitors for obesity treatment. DPP-4 inhibitors are an established drug class to improve glycemic control in patients with type 2 diabetes mellitus. Compounds with dual inhibitory activity in both MetAP2 and DPP-4 are desired. The present invention provides novel compounds with dual MetAP2 and DPP-4 inhibitition. These dual inhibitor compounds can be useful in the treatment of a MetAP2 and DPP-4 mediated condition. The present invention provides a compound of the following Formula (I); or a pharmaceutically acceptable salt thereof. In an embodiment of the invention, the compound is

6 Claims, No Drawings

PYRAZOLE COMPOUNDS

This invention relates to pyrazole compounds or pharmaceutically acceptable salts thereof. Compounds of this invention are inhibitors of methionine aminopeptidase 2 (MetAP2) and dipeptidyl peptidase-4 (DPP-4).

MetAP2 is a metalloproteinase that cleaves initiator methionine from nascent peptide emerging from the ribosomes. WO 2010/065879 reports small molecule MetAP2 inhibitors for obesity treatment.

DPP-4 inhibitors are an established drug class to improve glycemic control in patients with type 2 diabetes mellitus. Compounds with dual inhibitory activity in both MetAP2 and DPP-4 are desired.

The present invention provides novel compounds with dual MetAP2 and DPP-4 inhibitition. These dual inhibitor compounds can be useful in the treatment of a MetAP2 and DPP-4 mediated condition.

The present invention provides a compound of the Formula I

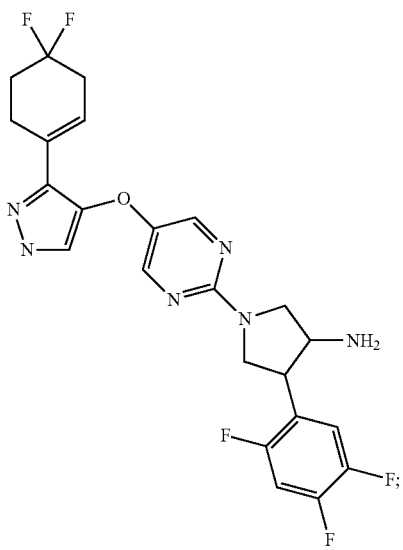

I or a pharmaceutically acceptable salt thereof.

In an embodiment of the invention, the compound is

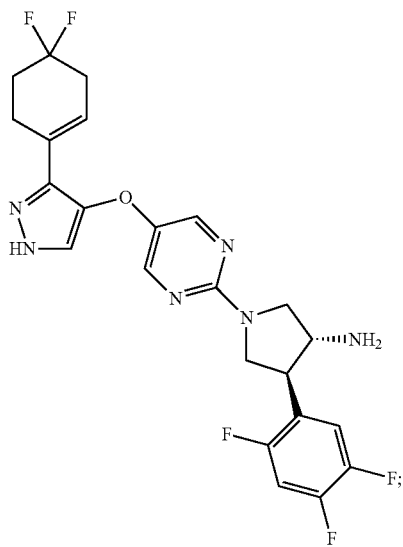

or a pharmaceutically acceptable salt thereof.

In an embodiment of the invention the compound is (3R,4S)-1-[5-[[3-(4,4-Difluorocyclohexen-1-yl)-1H-pyrazol-4-yl]oxy]pyrimidin-2-yl]-4-(2,4,5-trifluorophenyl)pyrrolidin-3-amine.

The invention provides a pharmaceutical composition comprising a compound of Formula I, or a pharmaceutically acceptable salt thereof, and at least one selected from the group consisting of a pharmaceutically acceptable carrier, diluent, and excipient.

The invention provides a method for treating type II diabetes in a mammal in need thereof, comprising administering to the mammal an effective amount of a compound of Formula I, or a pharmaceutically acceptable salt thereof. The invention provides a method for treating obesity in an mammal in need thereof, comprising administering to the mammal an effective amount of a compound of Formula I. In another embodiment, a compound of Formula I, or a pharmaceutically acceptable salt thereof for use in therapy. Further, provided is a compound of Formula I, or a pharmaceutically acceptable salt thereof, for use in the manufacture of a medicament.

Compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Additionally, certain intermediates described in the following preparations may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

The compounds of the present invention, or salts thereof, may be prepared by a variety of procedures known in the art, some of which are illustrated in the Preparations and Examples below. The specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

The abbreviations used herein are defined according to *Aldrichimica Acta*, Vol. 17, No. 1, 1984. Other abbreviations are defined as follows: "AMC" refers to 7-amido-4-methylcoumarin hydrobromide; "BSA" refers to Bovine Serum Albumin; "DIO" refers to diet induced obese; "EDTA" refers to ethylenediaminetetraacetic acid; "HEC" refers to hydroxy ethyl cellulose; "HEPES" refers to 4-(2-hydroxyethyl)-1-piperazineethanesulfonic acid; "HFD" refers to high fat diet; "HOAc" refers to acetic acid; "$IC_{50}$" refers to the concentration of an agent that produces 50% of the maximal inhibitory response possible for that agent; "MeOH" refers to methyl alcohol or methanol; "THF" refers to tetrahydrofuran and "Tris" refers to tris(hydroxymethyl) aminomethane.

PREPARATION 1

2-(2-Chloropyrimidin-5-yl)oxyacetonitrile

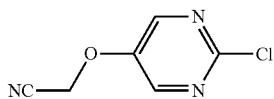

To a mixture of bromoacetonitrile (2.94 mL, 42.18 mmol), 2-chloropyrimidin-5-ol (5 g, 38.30 mmol) in $CH_3CN$ (100 mL) is added potassium carbonate (7.94 g, 57.45 mmol). The reaction mixture is heated to 60° C. for 2 hours. After cooling to room temperature, the solid is filtered and the filtrate is concentrated under reduced pressure. The residue is purified by silica gel flash chromatography eluting with a gradient of 100% ether to 1/1 ether/ethyl acetate to give the title compound (6 g, 35.38 mmol, 92.37%) as a white solid. Mass spectrum (m/z): 170 (M+H).

PREPARATION 2

2-(2-Chloropyrimidin-5-yl)oxy-3-oxo-propanenitrile

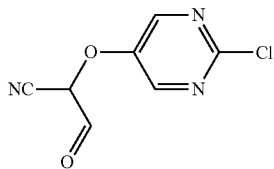 [SMILES: N#CC(C=O)Oc1cnc(Cl)nc1]

To a solution of 2-(2-chloropyrimidin-5-yl)oxyacetonitrile (6.00 g, 35.4 mmol) and ethyl formate (26.2 g, 354 mmol) in 1,2-dimethoxyethane (200 mL, 1930 mmol) is added potassium tert-butoxide (5.96 g, 53.1 mmol) portionwise at 0° C. The mixture is stirred at 85° C. overnight. The mixture is concentrated, dissolved in water (200 mL) and the pH is adjusted to pH~4 with HOAc. The water phase is extracted with ethyl acetate (5×200 mL). The combined organic phases are washed with water (2×500 mL), dried, and concentrated to give the title compound (6.10 g, 30.9 mmol, 87.3%) as a brown solid which is used without further purification. Mass spectrum (m/z): 196 (M–H).

Preparation 3

4-(2-Chloropyrimidin-5-yl)oxy-1H-pyrazol-3-amine

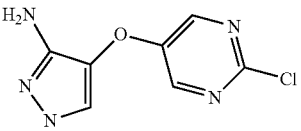 [SMILES: Nc1n[nH]cc1Oc1cnc(Cl)nc1]

To a solution of 2-(2-chloropyrimidin-5-yl)oxy-3-oxo-propanenitrile (6.00 g, 30.4 mmol) in acetic acid (20 mL) and ethanol (40 mL) is added hydrazine (64 mass %) in water (5.00 mL). The solution is stirred for 2 hours at 85° C., concentrated, and 7 N $NH_3$/MeOH (20 mL) is added. The mixture is stirred for 30 minutes and concentrated. The residue is purified by silica gel flash chromatography eluting with a gradient of 100% $CH_2Cl_2$ to 80% $CH_2Cl_2$ and 20% MeOH to give the title compound (3.15 g, 14.9 mmol, 49%) as an orange oil. Mass spectrum (m/z): 212 (M+H).

PREPARATION 4

5-[(3-Bromo-1H-pyrazol-4-yl)oxy]-2-chloro-pyrimidine

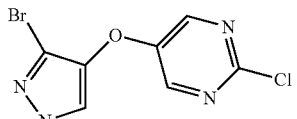

To a solution of tert-butyl nitrile (2.13 mL, 17.9 mmol) in $CH_3CN$ (100 mL) is added copper (I) bromide (2.56 g, 17.9 mmol). The mixture is stirred at room temperature for 1 hour under $N_2$, followed by the addition of 4-(2-chloropyrimidin-5-yl)oxy-1H-pyrazol-3-amine (3.15 g, 14.9 mmol) in $CH_3CN$ (10 mL). The mixture is stirred for 3 hours, concentrated and the residue is purified by silica gel flash chromatography eluting with a gradient of 100% $CH_2Cl_2$ to 80% $CH_2Cl_2$ and 20% MeOH to give the title compound (1.30 g, 4.72 mmol, 31.7%) as an orange oil. Mass spectrum (m/z): 275 (M+H).

PREPARATION 5

5-(3-Bromo-1-tetrahydropyran-2-yl-pyrazol-4-yl)oxy-2-chloro-pyrimidine

To a solution of 5-[(3-bromo-1H-pyrazol-4-yl)oxy]-2-chloro-pyrimidine (1.30 g, 1.30 g, 4.72 mmol) in THF (50 mL) are added 3,4-dihydro-2H-pran (2.15 mL, 23.6 mmol) and p-toluenesulfonic acid (0.246 g, 1.42 mmol). The mixture is stirred for 3 hours at 60° C., concentrated, and the residue is purified by silica gel flash chromatography eluting with a gradient of 100% petroleum ether to 1:1 petroleum ether/ethyl acetate to give the title compound (1.5 g, 4.2 mmol, 88%) as white solid. Mass spectrum (m/z): 259 (M+H).

PREPARATION 6 tert-Butyl N-[(3R,4S)-1-[5-(3-bromo-1-tetrahydropyran-2-yl-pyrazol-4-yl)oxypyrimidin-2-yl]-4-(2,4,5-trifluorophenyl)pyrrolidin-3-yl]carbamate

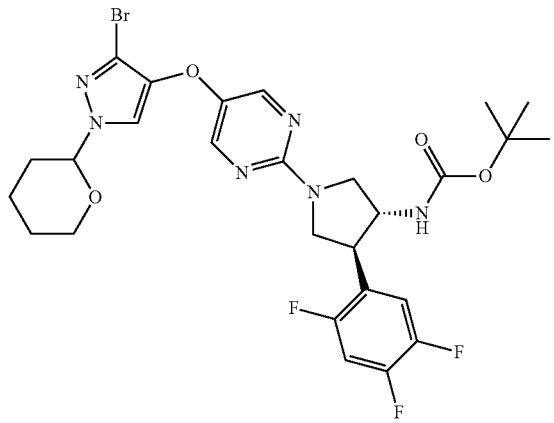 [SMILES: CC(C)(C)OC(=O)N[C@H]1CN(c2ncc(Oc3cn(C4CCCCO4)nc3Br)cn2)C[C@@H]1c1cc(F)c(F)cc1F]

A mixture of 5-(3-bromo-1-tetrahydropyran-2-yl-pyrazol-4-yl)oxy-2-chloro-pyrimidine (1.50 g, 4.17 mmol), tert-butyl N-[(3R,4S)-4-(2,4,5-trifluorophenyl)pyrrolidin-3-yl]carbamate (1.45 g, 4.59 mmol) and potassium carbonate (1.73 g, 12.5 mmol) in DMSO (20 mL) is stirred at 100° C. overnight. The mixture is cooled to room temperature, poured into water (100 mL), and extracted with ethyl acetate (3×100 mL). The combined organic extracts are washed with water (2×50 mL), dried, and concentrated. The residue is purified by silica gel flash chromatography eluting with a gradient of 100% CH$_2$Cl$_2$ to 80% CH$_2$Cl$_2$ and 20% MeOH to give the title compound (2.33 g, 3.64 mmol, 87.3%) as a yellow oil. Mass spectrum (m/z): 639 (M+H).

PREPARATION 7 tert-Butyl N-[(3R,4S)-1-[5-[3-(4,4-difluorocyclohexen-1-yl)-1-tetrahydropyran-2-yl-pyrazol-4-yl]oxypyrimidin-2-yl]-4-(2,4,5-trifluorophenyl)pyrrolidin-3-yl]carbamate

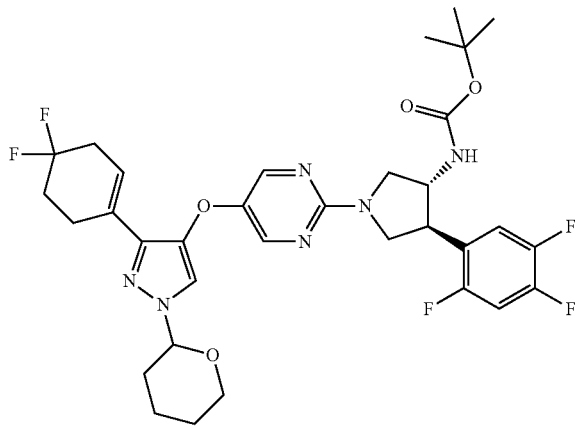 [SMILES: CC(C)(C)OC(=O)N[C@H]1CN(c2ncc(Oc3cn(C4CCCCO4)nc3C3=CCC(F)(F)CC3)cn2)C[C@@H]1c1cc(F)c(F)cc1F]

To a mixture of tert-butyl N-[(3R,4S)-1-[5-(3-bromo-1-tetrahydropyran-2-yl-pyrazol-4-yl)oxypyrimidin-2-yl]-4-(2,4,5-trifluorophenyl)pyrrolidin-3-yl]carbamate (2.33 g, 3.64 mmol), 2-(4,4-difluorocyclohexen-1-yl)-4,4,5,5-tetramethyl-1,3,2-dioxaborolane (1.07 g, 4.37 mmol), chloro(2-dicyclohexylphosphino-2',4',6'-triisopropyl-1,1'-biphenyl)[2-(2-aminoethyl)phenyl]palladium(II) (0.136 g, 0.182 mmol), 2-(dicyclohexylphosphino)-2',4',6'-triisopropylbiphenyl (0.177 g, 0.364 mmol) and potassium phosphate tribasic (1.59 g, 7.29 mmol) is added water (8 mL) and 1,4-dioxane (40 mL). The mixture is stirred at 110° C. under N$_2$ overnight. The mixture is concentrated and the residue is purified by silica gel flash chromatography eluting with a gradient of 100% CH$_2$Cl$_2$ to 80% CH$_2$Cl$_2$ and 20% MeOH to give the title compound (1.61 g, 2.38 mmol, 65.3%) as a pale-yellow foam. Mass spectrum (m/z): 677 (M+H).

EXAMPLE 1

(3R,4S)-1-[5-[[3-(4,4-Difluorocyclohexen-1-yl)-1H-pyrazol-4-yl]oxy]pyrimidin-2-yl]-4-(2,4,5-trifluorophenyl)pyrrolidin-3-amine

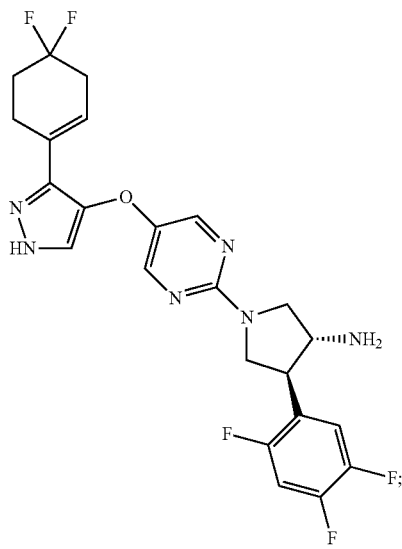 [SMILES: N[C@H]1CN(c2ncc(Oc3c[nH]nc3C3=CCC(F)(F)CC3)cn2)C[C@@H]1c1cc(F)c(F)cc1F]

To a solution of tert-butyl N-[(3R,4S)-1-[5-[3-(4,4-difluorocyclohexen-1-yl)-1-tetrahydropyran-2-yl-pyrazol-4-yl]oxypyrimidin-2-yl]-4-(2,4,5-trifluorophenyl)pyrrolidin-3-yl]carbamate (1.5 g, 2.2 mmol) in dichloromethane (10 mL, 156.0 mmol) is added trifluroacetic acid (10 mL) at room temperature. The mixture is stirred for 16 hours at room temperature and concentrated under reduced pressure. The residue is purified by silica gel flash chromatography eluting with a gradient of 100% CH$_2$Cl$_2$ (0.5% NH$_4$OH) to 90% CH$_2$Cl$_2$ (0.5% NH$_4$OH) 10% MeOH to give to give the title compound (1.02 g, 2.07 mmol, 93%) as a white foam. Mass spectrum (m/z): 493 (M+H), $^1$H NMR (CD$_3$OD) δ 2.09-2.20 (m, 2H), 2.64-2.75 (m, 4H), 3.33-3.36 (m, 1H), 3.48-3.60 (m, 2H), 3.69-3.75 (m, 1H), 4.03-4.13 (m, 2H), 6.27 (s, 1H), 7.17-7.41 (m, 3H), 8.19 (s, 2H).

Assays

Enzymatic Activity Assay of MetAP2 and MetAP1

The compound exemplified herein is tested essentially as described below and exhibits an IC$_{50}$ for the human and mouse MetAP2 assay of lower than or equal to 1000 nM and is considered selective for MetAP2 with a MetAP1 value greater than 30 μM.

Full length MetAP2 (human and mouse) and MetAP1 (human) proteins are generated from Sf9 cells using procedure similar to that described in Biochemistry 2003, 42, 5035-5042. MetAP2 and MetAP1 are purified in the presence of 5 mM $MnCl_2$ and 2 mM $CoCl_2$ respectively, and stored at −78° C. before use.

Inhibition of the catalytic activity of human and mouse MetAP2 by compounds in the present invention is measured by monitoring the formation of the product peptide (Gly-Lys-Val-Lys-Val-Gly-Val-Asn-Gly) from the substrate peptide (Met-Gly-Lys-Val-Lys-Val-Gly-Val-Asn-Gly) via LC/MS. The reaction is typically conducted by incubating the enzyme, test compound and substrate (150 μM) in a 100 μl assay buffer (50 mM HEPES, 100 mM NaCl, 50 mg/mL BSA, 0.17 mM Triton™ X-100 μl at pH 7.5) for 40 minutes. After the reaction is stopped by the addition of 200 μl $CH_3CN$, the levels of product and remaining substrate are quantified with a mass spectrometer. The activity of human MetAP1 is monitored by the formation of the fluorescent product rhodamine-methionine from the substrate methionine-rhodamine-methionine on a spectrophotometer with the excitation light at 460 nm and emission light at 535 nm. The reaction is typically conducted by incubating the enzyme, test compound and substrate (50 μM) in a 100 μl assay buffer (50 mM HEPES, 100 mM NaCl, 0.1% BSA, 0.05% Tween®-20, 50 μM $CoCl_2$) for 60 minutes. $IC_{50}$ value (concentration of test compound that provides 50% inhibition of MetAP2 activity) is calculated typically from a 10-point dose titration curve using a4-parameter equation.

The $IC_{50}$ for the human and mouse MetAP2 assay Example 1 is lower than 1000 nM and $IC_{50}$ for hMetAP1 is >30 μM, demonstrating selective MetAP2 inhibition as compared with MetAP1.

Enzymatic Activity Assay of DPP-4

Human DPP-4 ((39-766)-His) and mouse DPP-4 ((29-760)-His) are purified for use in the assay. The final concentration of hDPP-4 and mDPP-4 in the assay is 0.04 nM and 0.22 nM respectively.

Inhibition of the catalytic activity of human and mouse DPP-4 by the compound in the present invention is monitored by the formation of product fluorescence AMC (7-amido-4-methylcoumarin hydrobromide) from substrate Gly-Pro-AMC (Sigma, G2761) on an Envision plate reader. The reaction is typically conducted by incubating the enzyme, test compound, and substrate (10 μM) in a 75 μl assay buffer (0.01% BSA, 0.1 mM EDTA, 50 μM Tris-HCl, 0.01% Triton™-X100, 0.1 M NaCl at pH 7.5) for 30 minutes. After the reaction is stopped by the addition of 25 μl $ZnSO_4$ (10 mM), the formation of fluorescent product AMC is measured on an Envision plate reader with the excitation wavelength at 355 nm and emission wavelength at 460 nm. The $IC_{50}$ value is calculated typically from a 10-point dose titration curve using the 4-parameter logistic equation.

The $IC_{50}$ for Example 1 is lower than 1000 nM in the human and mouse DPP-4 assay and the results are shown in Table 1.

TABLE 1

Enzymatic activity of Example 1.

| Example # | hMetAP2 $IC_{50}$ (nM) | mMetAP2 $IC_{50}$ (nM) | hMetAP1 $IC_{50}$ (μM) | hDPP-4 $IC_{50}$ (nM) | mDPP-4 $IC_{50}$ (nM) |
|---|---|---|---|---|---|
| 1 | 9 ± 3 (n = 7) | 36 ± 34 (n = 5) | >30 | 6 ± 2 (n = 4) | 26 ± 11 (n = 4) |

Mean ± SEM (n);
SEM = standard error of the mean;
n = number of determination.

Therapeutic Weight Loss Effect Measurement of Compounds

To determine the therapeutic weight loss effects and improvement of metabolic parameters, the compound from the invention is tested in the high fat diet (HFD) feeding induced obese mouse model (DIO mice). In this model, C57/Bl6J male mouse is fed with the 60% HFD (D12492i, Research Diets) for 16~28 weeks to establish obesity with body weight reaching around 50 g. The mice will gradually increase the body weight to about 50 g and maintain that weight in this obese state. Test compound (via the vehicle of 0.5% HEC plus 0.25% Tween®-80 at 5 mL/kg) is administered orally to the obese DIO mice once or twice daily throughout the study duration. The dose-dependent weight loss of obese DIO mice for Example 1 of the oral treatment at 20 mg/kg and 60 mg/kg once daily is about 4% and 17% weight loss compared to the vehicle group at day 14, respectively. The data support that the compound of Example 1 is associated with desired weight loss and could offer a therapeutic weight loss effect.

DPP-4 Pharmacodynamics Assay in Mouse

To determine the in vivo DPP-4 inhibition by MetAP2 plus DPP-4 dual inhibitor compounds, C57B/L6 lean mice are administrated with the compound in fed states and then DPP-4 target engagement in plasma is measured.

Animals are weighed and randomized by body weight. Each mouse is dosed via oral gavage with vehicle or testing compound formulated with vehicle for up to 3 times. The first dose is administered at 9~10 am on day 1. The second dose is administered at 16:30~17:30 on day 1. The third dose is administered at 9~10 am on day 2. The mice are fasted for 6 hours after the last dose before termination at ~3 μm on day 2. Blood samples are collected at 1 hour after the first dosing and upon termination. EDTA-$K_2$ at final concentration of 5 mM is used as an anticoagulant. Plasma, isolated from the blood samples, is used to determine the plasma DPP-4 enzyme activity.

Plasma DPP-4 enzyme activity in the present invention is monitored by the formation rate of fluorescence AMC from substrate Gly-Pro-AMC (Sigma, G2761) via Envision plate reader. The reaction is typically conducted by incubating the plasma (20 μl) and substrate (10 μM) in a 40 μL assay buffer (0.01% BSA, 0.1 mM EDTA, 50 μM Tris-HCl, 0.01% Triton™-X100, 0.1 M NaCl at pH 7.5). Fluorescence signal is read immediately after the start of the reaction in kinetic model in Envision plate reader. The excitation wavelength is set at 355 nm and emission wavelength is set at 460 nm. The plasma DPP-4 activity is calculated from reaction velocity. The percentage plasma DPP-4 inhibition is normalized against plasma DPP-4 activity in the vehicle group, which is set as 0% inhibition.

The plasma DPP-4 inhibition for Example 1 under the assay condition is 86% and 83% for 1 hour after the first dosing and upon termination, respectively. The data support that the compound of Example 1 is associated with desired DPP-4 inhibition that could yield therapeutic glycemic control.

We claim:

1. A compound of the Formula

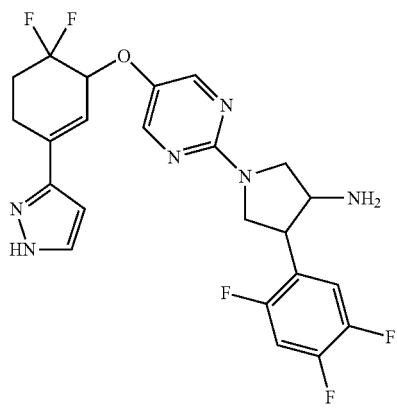 [SMILES: NC1CN(c2ncc(OC3C=C(c4cc[nH]n4)CCC3(F)F)cn2)CC1c1cc(F)c(F)cc1F]

or a pharmaceutically acceptable salt thereof.

2. A compound as claimed by claim 1 wherein the compound is

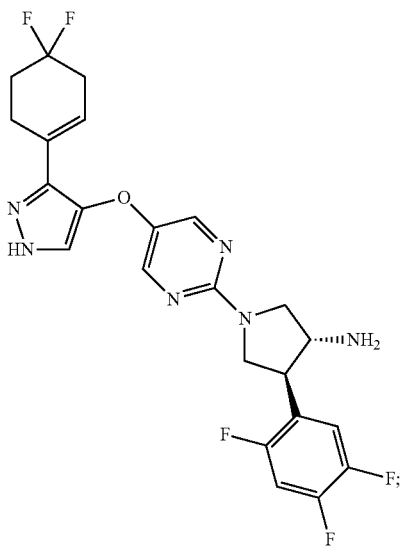 [SMILES: N[C@H]1CN(c2ncc(Oc3c[nH]nc3C3=CCC(F)(F)CC3)cn2)C[C@@H]1c1cc(F)c(F)cc1F]

or a pharmaceutically acceptable salt thereof.

3. A compound or salt as claimed by claim 1 wherein the compound is (3R,4S)-1-[5-[[3-(4,4-Difluorocyclohexen-1-yl)-1H-pyrazol-4-yl]oxy]pyrimidin-2-yl]-4-(2,4,5-trifluorophenyl)pyrrolidin-3-amine.

4. A pharmaceutical composition comprising a compound as claimed by claim 1, or a pharmaceutically acceptable salt thereof, and at least one of a pharmaceutically acceptable carrier, diluent, or excipient.

5. A method for treating type II diabetes in a mammal in need thereof, comprising administering to the mammal an effective amount of a compound, or a pharmaceutically acceptable salt thereof, as claimed by claim 1.

6. A method for treating obesity in a mammal in need thereof, comprising administering to the mammal an effective amount of a compound, or pharmaceutically acceptable salt thereof, as claimed by claim 1.

* * * * *

UNITED STATES PATENT AND TRADEMARK OFFICE
CERTIFICATE OF CORRECTION

PATENT NO. : 9,822,101 B1
APPLICATION NO. : 15/535817
DATED : November 21, 2017
INVENTOR(S) : Koc Kan Ho et al.

Page 1 of 1

It is certified that error appears in the above-identified patent and that said Letters Patent is hereby corrected as shown below:

On the Title Page

Abstract, Column 2, Line 13 - delete "inhibitition" and insert --inhibition--

Signed and Sealed this
Twenty-ninth Day of May, 2018

Andrei Iancu
*Director of the United States Patent and Trademark Office*